US00PP20594P2

(12) United States Plant Patent
Blom

(10) Patent No.: US PP20,594 P2
(45) Date of Patent: Dec. 22, 2009

(54) ***ECHINACEA* PLANT NAMED 'MILKSHAKE'**

(50) Latin Name: *Echinacea purpurea*
Varietal Denomination: Milkshake

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 12/228,279

(22) Filed: Aug. 11, 2008

(51) Int. Cl.
*A01H 5/00* (2006.01)

(52) U.S. Cl. ..... Plt./428
(58) Field of Classification Search ..... Plt./428
See application file for complete search history.

*Primary Examiner*—June Hwu
(74) *Attorney, Agent, or Firm*—C. A. Whealy

(57) ABSTRACT

A new and distinct cultivar of *Echinacea* plant named 'Milkshake', characterized by its upright and columnar plant habit; moderately vigorous growth habit; strong and thick flowering stems; freely basal branching habit; and large anemone-type inflorescences with white-colored ray florets and yellow green-colored disc florets.

3 Drawing Sheets

Botanical designation: *Echinacea purpurea.*
Cultivar denomination: 'Milkshake'.

BACKGROUND OF THE INVENTION

The present invention relates to a new and distinct cultivar of *Echinacea* plant, botanically known as *Echinacea purpurea,* and hereinafter referred to by the name 'Milkshake'.

The new *Echinacea* plant is a product of a planned breeding program conducted by the Inventor in IJsselstein and Zuidwolde, The Netherlands. The objective of the breeding program is to create new *Echinacea* cultivars with attractive inflorescence form and floret coloration.

The new *Echinacea* originated from a cross-pollination in 2004 by the Inventor in IJsselstein, The Netherlands of a proprietary selection of *Echinacea purpurea* identified as code number Ec 302-16, not patented, as the female, or seed, parent with a proprietary selection of *Echinacea purpurea* identified as code number Ec 204-01, not patented, as the male, or pollen, parent. The new *Echinacea* was discovered and selected by the Inventor as a single flowering plant from within the progeny of the stated cross-pollination grown in a controlled greenhouse environment in Zuidwolde, The Netherlands in July, 2006.

Asexual reproduction of the new *Echinacea* plant by micropropagation a controlled greenhouse environment in Enkhuizen, The Netherlands since February, 2007, has shown that the unique features of this new *Echinacea* plant are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Milkshake'. These characteristics in combination distinguish 'Milkshake' as a new and distinct cultivar of *Echinacea:*

1. Upright and columnar plant habit.
2. Moderately vigorous growth habit.
3. Strong and thick flowering stems.
4. Freely basal branching habit.
5. Large anemone-type inflorescences with white-colored ray florets and yellow green-colored disc florets.

Plants of the new *Echinacea* plant can be compared to plants of the female parent selection. Plants of the new *Echinacea* plant differ from plants of the female parent selection in the following characteristics:

1. Plants of the new *Echinacea* are more freely branching than plants of the female parent selection.
2. Plants of the new *Echinacea* have smaller inflorescences than plants of the female parent selection.
3. Plants of the new *Echinacea* and the female parent selection differ in ray floret color as plants of the female parent selection have pink-colored ray florets.

Plants of the new *Echinacea* plant can be compared to plants of the male parent selection. Plants of the new *Echinacea* plant differ from plants of the male parent selection in the following characteristics:

1. Plants of the new *Echinacea* are taller than plants of the male parent selection.
2. Plants of the new *Echinacea* have stronger stems than plants of the male parent selection.

Plants of the new *Echinacea* can be compared to plants of *Echinacea purpurea* 'Coconut Lime', disclosed in U.S. Plant Pat. No. 18,617. In side-by-side comparisons conducted in Zuidwolde, The Netherlands, plants of the new *Echinacea* differed from plants of 'Coconut Lime' in the following characteristics:

1. Plants of the new *Echinacea* were taller than plants of 'Coconut Lime'.
2. Plants of the new *Echinacea* were more freely branching than plants of 'Coconut Lime'.
3. Plants of the new *Echinacea* and 'Coconut Lime' differed in floret coloration.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea*.

The photograph on the first sheet comprises a side perspective view of a typical flowering plant of 'Milkshake' grown in an outdoor nursery.

The photograph on the second sheet is a close-up view of a typical flowering stem of 'Milkshake'.

The photograph at the top of the third sheet is a close-up view of a typical inflorescence of 'Milkshake'.

The photograph at the bottom of the third sheet is a close-up view of a typical leaf and inflorescence bud of 'Milkshake'.

DETAILED BOTANICAL DESCRIPTION

The following observations and measurements describe plants grown in Zuidwolde, The Netherlands during the summer in an outdoor nursery and under conditions and practices which approximate those generally used in commercial *Echinacea* production. During the production of the plants, day temperatures ranged from 12° C. to 30° C. and night temperatures ranged from 3° C. to 16° C. Measurements and numerical values represent averages for typical flowering plants. Plants were two years from planting when the photographs and description were taken. In the following description, color references are made to The Royal Horticultural Society Colour Chart, 2001 Edition, except where general terms of ordinary dictionary significance are used.

Botanical classification: *Echinacea purpurea* 'Milkshake'.

Parentage:

*Female parent.*—Proprietary selection of *Echinacea purpurea* identified as code number Ec 302-16, not patented.

*Male parent.*—Proprietary selection of *Echinacea purpurea* identified as code number Ec 204-01, not patented.

Propagation:

*Type.*—By micropropagation.

*Time to initiate roots.*—About one week at 25° C.

*Time to produce a rooted young plant.*—About five weeks at 21° C.

*Root description.*—Fine, fibrous; pale creamy white in color.

*Rooting habit.*—Freely branching; moderately dense.

Plant description:

*Plant form/growth habit.*—Upright and columnar plant habit; freely basal branching with about nine basal branches developing per plant. Moderately vigorous growth habit.

*Plant height.*—About 81.8 cm.

*Plant diameter or spread.*—About 45.3 cm.

*Basal branches.*—Length: About 51.1 cm. Diameter: About 7.5 mm. Internode length: About 3 cm. Aspect: Upright. Strength: Strong. Texture: Pubescent; rough. Color: Close to 144A.

Foliage description:

*Arrangement.*—Alternate, simple.

*Length.*—About 9.9 cm.

*Width.*—About 4.2 cm.

*Shape.*—Narrowly ovate to ovate.

*Apex.*—Acute.

*Base.*—Attenuate.

*Margin.*—Entire, sinuate.

*Texture, upper and lower surfaces.*—Pubescent; rough.

*Venation pattern.*—Pinnate.

*Color.*—Developing leaves, upper surface: Close to 137A. Developing leaves, lower surface: Close to 137B. Fully expanded leaves, upper surface: Close to 137A; venation, close to 145C to 145D. Fully expanded leaves, lower surface: Close to 138B; venation, close to 145B to 145C.

*Petioles.*—Length: About 3.3 cm. Diameter: About 3 mm. Texture, upper surface: Smooth, glabrous. Texture, lower surface: Sparsely pubescent. Color, upper surface: Close to 145B. Color, lower surface: Close to 145A to 145B.

Inflorescence description:

*Appearance.*—Rotate anemone-type inflorescence form with ray and disc florets arranged acropetally on a capitulum. Inflorescences positioned above the foliage on strong and thick peduncles facing upright.

*Quantity of inflorescences per plant.*—About seven open inflorescences and buds develop per flowering stem.

*Fragrance.*—Faint; pleasant, sweet.

*Time to flower.*—Plants flower continuously from late June to late September in The Netherlands.

*Inflorescence longevity.*—Inflorescences maintain good substance for about three weeks on the plant; inflorescences not persistent.

*Inflorescence bud.*—Height: About 1.6 cm. Diameter: About 2.3 cm. Shape: Flattened globular. Color: Darker than 143A.

*Inflorescence size.*—Diameter: About 7.8 cm. Depth (height): About 6.8 cm. Disc diameter: About 6.4 cm. Receptacle height: About 1.6 cm. Receptacle diameter: About 1.7 cm. Receptacle color: Between 155C and 157D.

*Ray florets.*—Length: About 4.7 cm. Width: About 1.3 cm. Shape: Oblanceolate. Apex: Praemorse. Base: Cuneate. Margin: Entire. Texture, upper and lower surfaces: Smooth, glabrous; longitudinally ridged. Number of ray florets per inflorescence: About 28 arranged in about two whorls. Aspect: Horizontal to reflexing. Color: When opening, upper surface: Close to 157A; towards the apex, close to 145B to 145C. When opening, lower surface: Close to 150C; towards the apex, close to 150B; towards the base, close to 145A to 145B. Fully opened, upper surface: Close to 157A; towards the apex, close to 145B to 145C. Fully opened, lower surface: Close to 145C, color; towards the apex and base, close to 145A to 145B; towards the margins, close to 150D.

*Disc florets.*—Length: About 1.8 cm. Diameter: About 1 cm. Shape: Tubular, enlarged; apices acute. Number of disc florets per inflorescence: About 450. Texture, upper and lower surfaces: Smooth, glabrous. Color: Immature, inner surface: Close to 145D; towards the apex, close to 145C. Immature, outer surface: Close to 145B. Mature, inner surface: Close to 157D; towards the apex, close to N144B. Mature, outer surface: Close to 150C to 150D; towards the apex, close to N144B.

*Receptacle spines.*—Quantity: One per disc floret. Shape: Acicular. Apex: Acute. Base: Attenuate. Texture: Smooth, glabrous. Color: Apex: Close to 24A. Mid-section: Close to 144A. Base: Close to 145C to 145D.

*Involucral bracts.*—Quantity per inflorescence: About 60 in about three whorls. Length: About 9 mm. Width: About 3 mm. Shape: Narrowly ovate. Apex: Acute. Base: Cuneate. Margin: Entire. Texture, upper surface: Smooth, glabrous. Texture, lower surface: Pubescent. Color, upper surface: Close to 137A. Color, lower surface: Close to 137B.

*Peduncles.*—Length: About 19.3 cm. Diameter: About 4 mm. Strength: Strong. Aspect: Mostly upright. Texture: Pubescent; rough. Color: Close to 144B to 144C.

*Reproductive organs.*—Androecium (present on disc florets only): Quantity per floret: About five. Filament length: About 2 mm. Filament color: Close to 164D. Anther shape: Oblong. Anther length: About 2 mm. Anther color: Close to 165B. Pollen amount: None observed. Gynoecium (present on disc and ray florets): Quantity per floret: One. Pistil length: About 7 mm. Stigma shape: Elongate. Stigma color: Close to 148C to 148D. Style length: About 6.5 mm. Style color: Close to 150D. Ovary color: Close to 157D. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind, have been observed to tolerate temperatures ranging from about −20° C. to about 35° C.

It is claimed:

1. A new and distinct *Echinacea* plant named 'Milkshake' as illustrated and described.

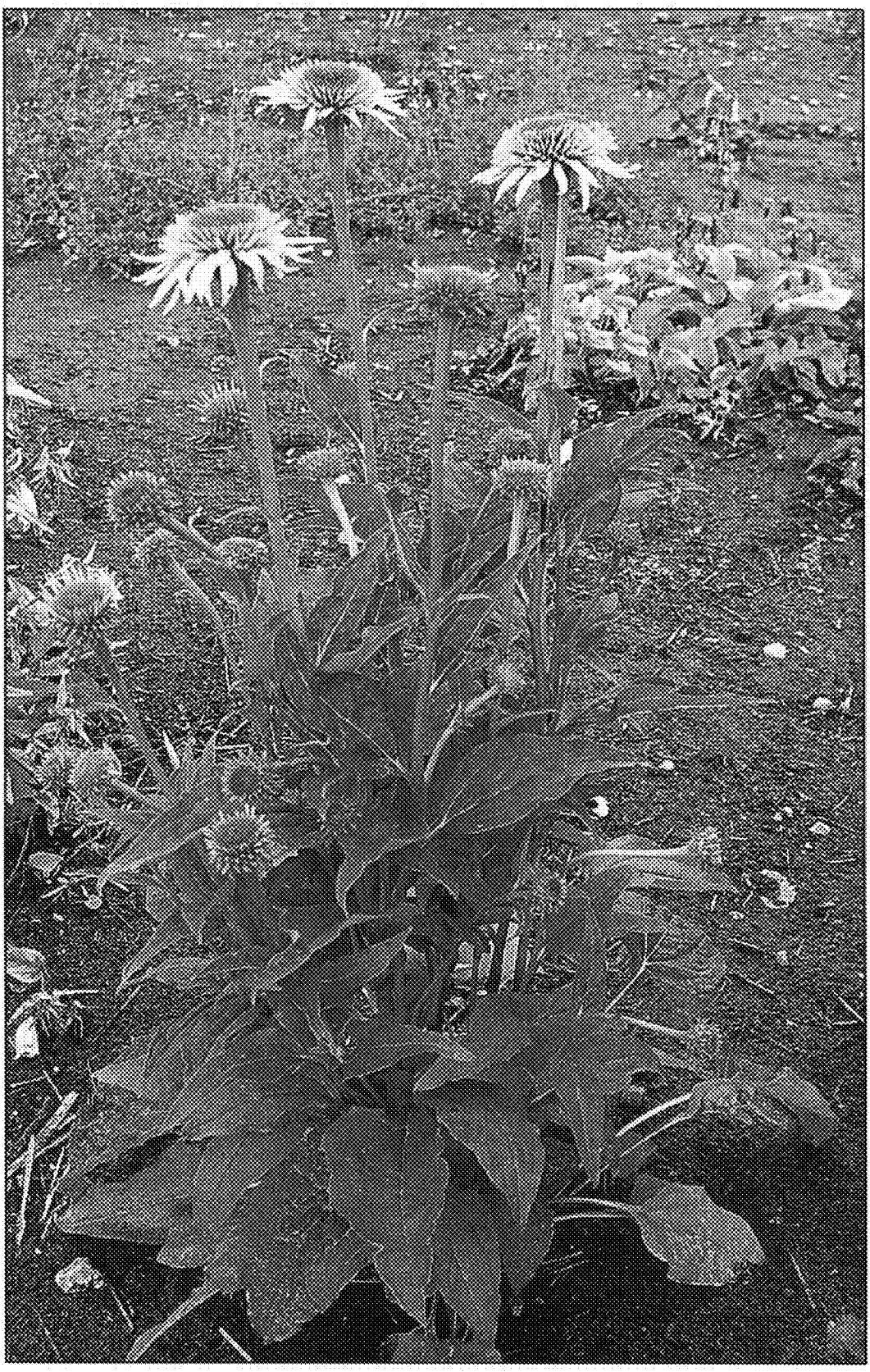

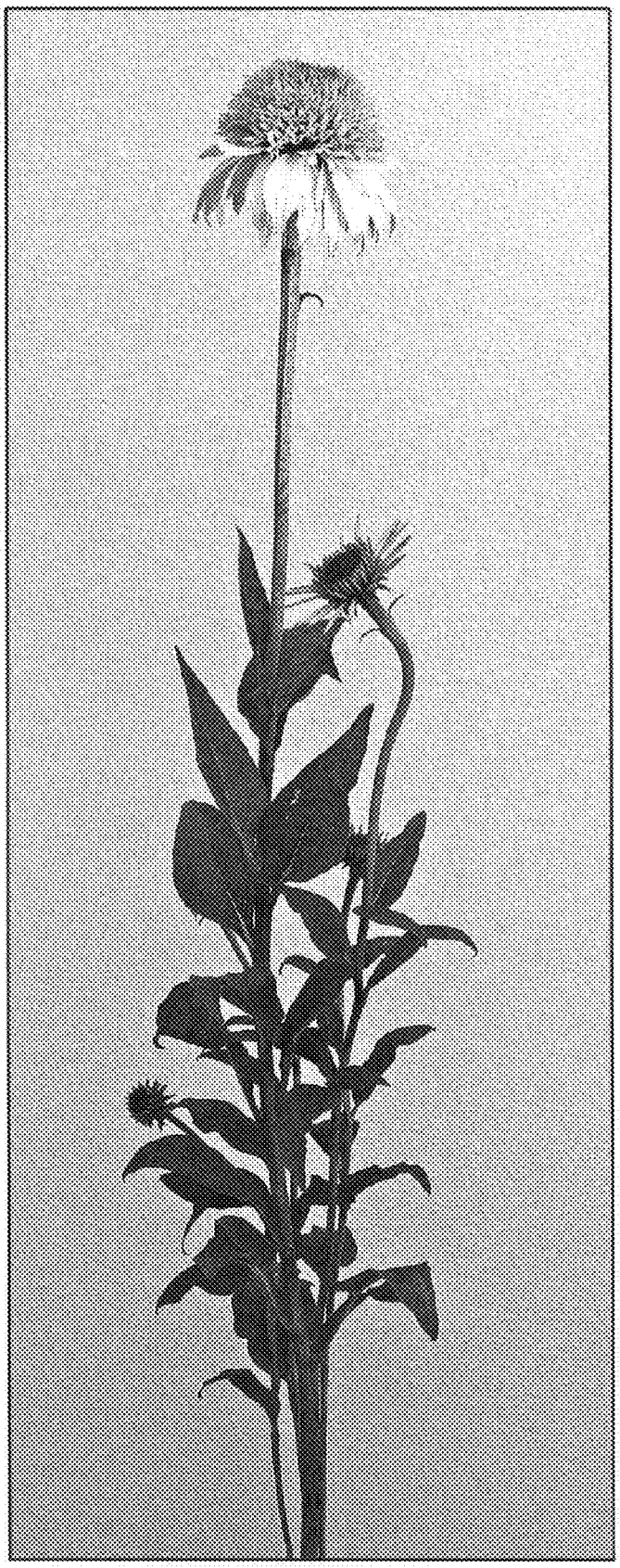

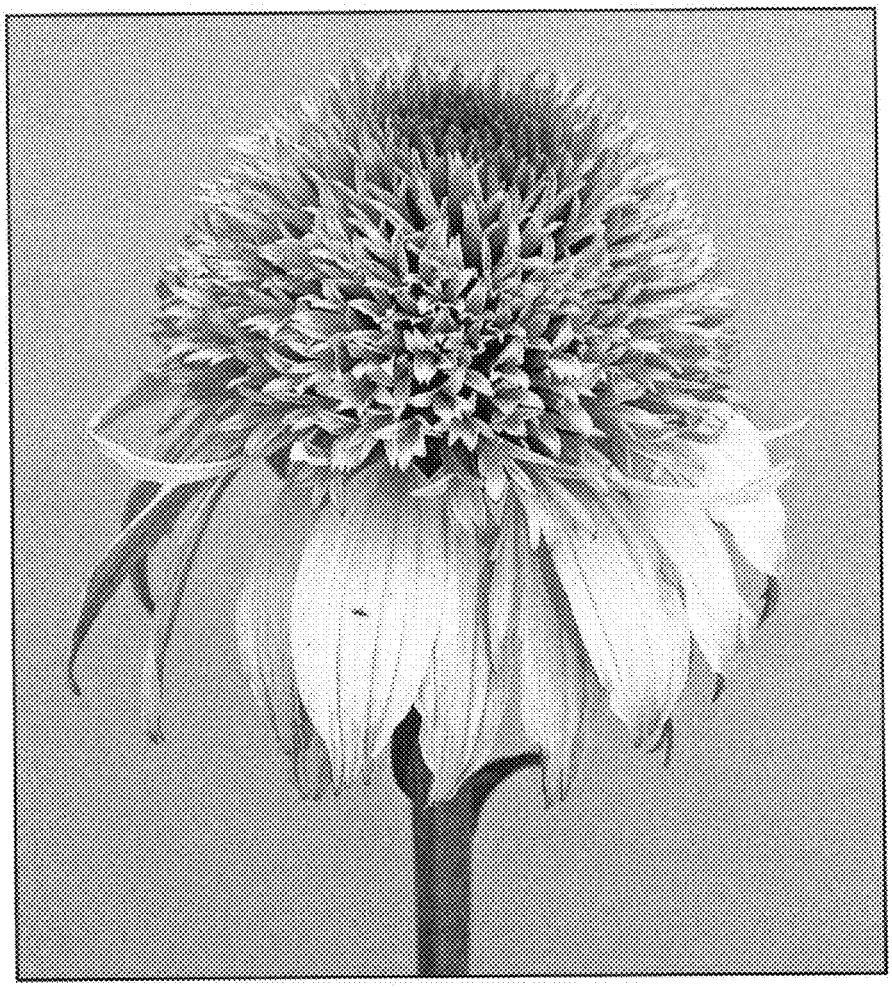
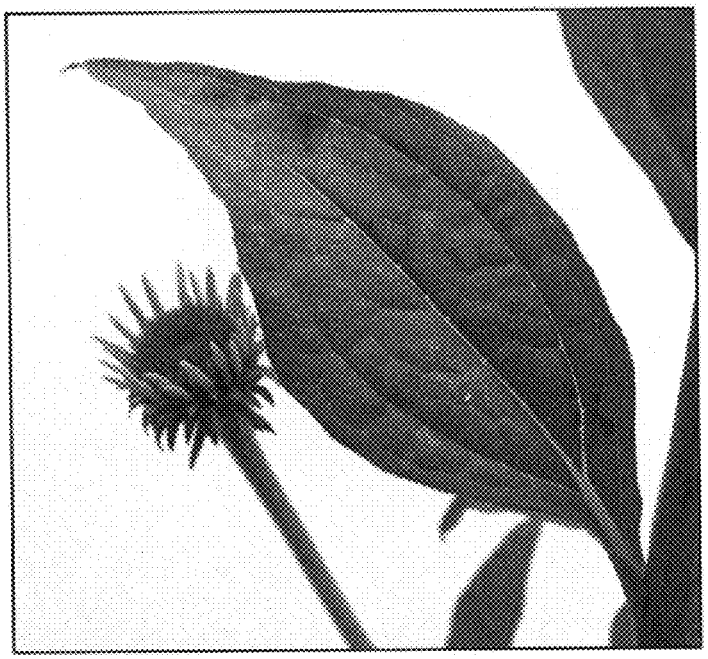

* * * * *